(12) United States Patent
Moses

(10) Patent No.: US 8,028,703 B1
(45) Date of Patent: Oct. 4, 2011

(54) SLEEP MOUTHPIECE

(75) Inventor: Allen J. Moses, Chicago, IL (US)

(73) Assignee: Moses Appliance, LLC, Chicago, IL (US)

(*) Notice: Subject to any disclaimer, the term of this patent is extended or adjusted under 35 U.S.C. 154(b) by 0 days.

(21) Appl. No.: 12/861,470

(22) Filed: Aug. 23, 2010

(51) Int. Cl.
*A61J 17/00* (2006.01)
*A61F 5/56* (2006.01)

(52) U.S. Cl. ......... 128/848; 606/234; 606/235; 606/236

(58) Field of Classification Search .................. 128/848, 128/859–862, 207.14; 433/6–7; 606/234–236; 215/11.5, DIG. 3
See application file for complete search history.

(56) References Cited

U.S. PATENT DOCUMENTS

| | | | |
|---|---|---|---|
| 587,358 | A | 8/1897 | Anderson |
| 4,862,903 | A | 9/1989 | Campbell |
| 5,117,816 | A | 6/1992 | Shapiro et al. |
| 5,381,783 | A | 1/1995 | Hintz |
| 5,536,168 | A * | 7/1996 | Bourke .............................. 433/6 |
| 5,715,840 | A | 2/1998 | Hall |
| 5,792,067 | A | 8/1998 | Karell |
| 5,941,247 | A | 8/1999 | Keane |
| 6,055,986 | A | 5/2000 | Meade |
| 6,494,209 | B2 | 12/2002 | Kulick |
| 6,619,290 | B1 | 9/2003 | Zacco |
| 6,820,617 | B2 | 11/2004 | Robertson et al. |
| 7,607,438 | B2 * | 10/2009 | Pelerin .......................... 128/859 |
| 2004/0103905 | A1 * | 6/2004 | Farrell .......................... 128/861 |
| 2007/0068534 | A1 * | 3/2007 | Bailey et al. ................... 128/848 |
| 2010/0180900 | A1 * | 7/2010 | Talsma et al. ............. 128/207.14 |

* cited by examiner

*Primary Examiner* — Patricia Bianco
*Assistant Examiner* — Ophelia Hawthorne
(74) *Attorney, Agent, or Firm* — McAndrews, Held & Malloy, Ltd.

(57) ABSTRACT

Sleep mouthpieces are provided. One such mouthpiece includes an intraoral component including first and second troughs configured to receive a user's upper and lower teeth or ridges. The troughs are separated by a distance, thereby providing an opening that can allow mouth breathing. The mouthpiece includes an extraoral component connected to the intraoral component by first and second columns. The columns can be positioned at first and second ends of the intraoral component. The columns can also be positioned at first and second ends of the opening. The columns can also be positioned between the ends of the opening and the ends of the intraoral component. The extraoral component includes first and second retention portions extending from the first and second columns away from a center of the intraoral component and away from the opening. The first and second retention portions are configured to contact the user's face.

20 Claims, 5 Drawing Sheets

SLEEP MOUTHPIECE

CROSS-REFERENCE TO RELATED APPLICATIONS/INCORPORATION BY REFERENCE

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Snoring is a common sleep disturbance, affecting both sexes and persons of all ages. Snoring is more often observed in men but is also highly prevalent in pregnant women. Snoring is often a symptom of obstructive sleep apnea (OSA), a disorder having serious comorbid symptoms. Upper airway resistance is a symptom that is often part of the continuum of OSA. OSA is characterized by repeated arousals from sleep. Symptoms of OSA, in fact, can be found in non-snorers. Edentulous people having old (worn down) dentures or people sleeping without their full denture also commonly snore and have OSA. Snorers, including pregnant women, can be screened for sleep breathing disorders. Such disorders can be treated using methods that are low cost, benign, non-invasive, drug-free and comfortable.

By the third trimester of pregnancy, 97% of women report sleep disturbances. Sharma S., Franco R., Sleep and its Disorders in Pregnancy, Wisconsin Medical Journal, 2004, 103 (5) 48-52. It has been reported that as high as 46% of pregnant women snore in the third trimester. Sullivan C., Edwards N., Sleep-Disordered Breathing in Pregnancy in Randerath W J, Sanner B M, Somers V K (eds): Sleep Apnea, Prog Respir Res. Basel, Karger, 2006, vol 35, pp 224-237. "Pregnancy Associated Sleep Disorders" is now recognized as a distinct clinical entity in the International Classification of Sleep Disorders Manual (ICSD, DSM IV). American Academy of Sleep Medicine, International classification of sleep disorders, 2nd ed.: Diagnosis and coding manual, Westchester, IL: American Academy of SleepMedicine; 2005. 148-152. The spectrum of sleep disturbances in pregnant women ranges from increased incidence of insomnia, nocturnal awakening, nocturia, parasomnias (especially restless leg syndrome), to snoring and OSA. Sahota P. K., Jain S. S., Dhand R., Sleep Disorders In Pregnancy, Sleep and Respiratory Neurobiology, 2003; 9(6) 477-483.

It is generally agreed that pregnant women snore more than those who are not pregnant. In fact, a study reported frequent loud snoring in 14% of the pregnant women vs. 4% in the group of non-pregnant women. Loube D. I., Poceta S., Morales M. C., Peacock M. D., Mitler M. M., Self-Reported Snoring In Pregnancy: Association With Fetal Outcome, Chest, 1996; 109:885-89. Snoring may be a sign of pregnancy-induced hypertension. Franklin K. A., Holmgren P. A., Jonsson F., Poromaa N., Stenlund H., Svanborg E., Snoring, Pregnancy-Induced Hypertension, And Growth Retardation Of The Fetus, Chest, 2000 117:137-141.

Sleep disordered breathing is significantly more prevalent in obese pregnant women than pregnant women based on what is considered normal weight. Maasilta P., Bachour A., Teramo K., Polo O., Laitnen L. A., Sleep-Related Disordered Breathing During Pregnancy In Obese Women, Chest. 2001; 120(5):1448-1454. With the ongoing epidemic of obesity in the general population, obese pregnant woman may become the norm (the most common patient type).

A study has revealed that snoring pregnant women had a 2-fold greater incidence of hypertension, preeclampsia, intrauterine growth restriction and lower Apgar scores at birth. Franklin K. A., Holmgren P. A., Jonsson F., Poromaa N., Stenlund H., Svanborg E., Snoring, Pregnancy-Induced Hypertension, And Growth Retardation Of The Fetus, Chest, 2000 117:137-141. Pregnancy may precipitate or worsen OSA. Kowall J., Clark G., Nino-Murcia G., Powell N., Precipitation Of Obstructive Sleep Apnea During Pregnancy, Obstet Gynecol. 1989; 74: 453-455. OSA may also be a cause of fetal compromise. Sahin F. K., Gulengal K., Cosar E., Saylan F., Fidan F., Yilmazer M., Unlu M., Obstructive Sleep Apnea In Pregnancy And Fetal Outcome, Obste & Gyne Survey, 2008(5):292-293.

It is during the third trimester of pregnancy that these respiratory changes during sleep markedly increase the incidence and severity of sleep disordered breathing Edwards N., Middleton P. G., Blyton D. M., Sullivan C. E., Sleep Disordered Breathing And Pregnancy, Thorax, 2002(57):555-558. There is a 20% reduction in functional residual capacity and maternal oxygenation is decreased. Weinberger S. E., Weiss S. T., Cohen W. R., et al. State Of The Art: Pregnancy And The Lung, Am Rev Resp Dis; 1980; 121:559-581. Increased airway collapsibility during tidal ventilation increases susceptibility to snoring and OSA. Remmers J. E., deGroot W. J., Sauerland E. K., Anch A. M., Pathogenesis Of Upper Airway Occlusion During Sleep, J. Appl. Physiol. 1978; 44:931-938. This effect is exacerbated in the supine position. Edwards N., Middleton P. G., Blyton D. M., Sullivan C. E., Sleep Disordered Breathing and Pregnancy, Thorax, 2002(57):555-558. 42% of pregnant women at 36 weeks gestation reported chronic nasal congestion and rhinitis. Bende M., Gredmark T., Nasal Stuffiness During Pregnancy, Laryngoscope 1999; 109:1108-1110.

Snoring alone is not a good marker for OSA in pregnant women. Snoring alone however may decrease the overall sleep quality of the mother-to-be and be a serious detriment to good sleep quality of the sleep partner. The combination of snoring and witnessed apneas provides a more reliable diagnostic screening tool for OSA.

In light of the above, it is desirable that pregnant women be screened for sleep disordered breathing. However, a full night polysomnographic evaluation can be onerous and unduly burdensome for a woman in her third trimester. Ambulatory home polysomnographic testing is an easy and benign alternative to a night totally wired up in a sleep lab, but does not have equivalent diagnostic accuracy.

OSA related to pregnancy appears to be self-limiting to the third trimester. The snoring and OSA usually discontinue with delivery of the baby and subsequent weight loss.

Existing treatments include intraoral mouthpieces and Continuous Positive Airway Pressure (CPAP) devices. However, known intraoral mouthpieces can be bulky, may cause discomfort, are generally more expensive and usually need fitting by a dentist. Also, CPAP requires attachment to devices, thereby inhibiting frequent positional changes during sleep. Pregnant women, having a difficult time finding a comfortable position, shift around often during sleep. Pregnant women also have enough hormonal, postural and psychological burdens to deal with that CPAP usually becomes an intolerable alternative.

In light of the foregoing, there is a need for an improved snoring treatment that can provide improved comfort.

SUMMARY OF THE INVENTION

Embodiments of the present technology provide sleep mouthpieces configured to treat snoring. In an embodiment, such a mouthpiece includes: an intraoral component comprising first and second troughs, the troughs substantially vertically aligned and configured to receive a user's upper and lower teeth or upper and lower ridges, the troughs separated by a distance, thereby providing an opening through which the user can breathe; and an extraoral component connected to the intraoral component by a first column and a second column, the first column positioned at a first end of the intraoral component and the second column positioned at a second end of the intraoral component, the extraoral component including a first retention portion that extends from the first column away from a center of the intraoral component, the extraoral component further including a second retention portion that extends from the second column away from the center of the intraoral component, the first and second retention portions of the extraoral component configured to contact the user's face.

In certain embodiments, the troughs are configured to span only between the user's cuspid teeth areas.

In certain embodiments, the troughs are configured to span only across the user's anterior ridges, and not to span across the user's posterior ridges.

In certain embodiments, the first column is positioned between the user's upper and lower cuspid teeth area on a first side of the user's mouth, and the second column is positioned between the user's upper and lower cuspid teeth area on the other side of the user's mouth.

In certain embodiments, the opening is positioned between the user's upper and lower cuspid teeth areas.

In certain embodiments, the first and second retention portions each comprise a ring.

In certain embodiments, the first and second columns each extend a length between the intraoral component and the extraoral component, the length being sufficient to accommodate the thickness of the user's lips, the length being greater than about 8 millimeters.

In certain embodiments, the first and second columns each extend from a corner of the user's mouth.

In certain embodiments, the mouthpiece further includes a first vertical support column and a second vertical support column configured to separate the troughs by the distance.

In certain embodiments, the intraoral component includes a plurality of protrusive dots about the periphery of a lingual side of the opening.

In certain embodiments, the mouthpiece further includes a band attachable to the extraoral component, the band configured to maintain the intraoral component in the user's mouth during sleep.

In certain embodiments, the mouthpiece is symmetrical such that either trough can accommodate the user's upper teeth or ridge and either trough can accommodate the user's lower teeth or ridge.

In certain embodiments, the extraoral component does not interfere with the user's ability to open or close the user's lips.

In certain embodiments, the positioning of the user's upper and lower teeth or ridges in the troughs provides for improved airway patency, such that the user's airway is larger than when the user's mandible is in a normal sleep position.

In an embodiment, a mouthpiece includes: an intraoral component comprising first and second troughs, the troughs substantially vertically aligned and configured to receive a user's upper and lower teeth or upper and lower ridges, the troughs separated by a distance, thereby providing an opening through which the user can breathe; and an extraoral component connected to the intraoral component by a first column and a second column, the first column positioned at a first end of the opening and the second column positioned at a second end of the opening, the extraoral component including a first retention portion that extends from the first column away from the opening, the extraoral component further including a second retention portion that extends from the second column away from the opening, the first and second retention portions of the extraoral component configured to contact the user's face.

In an embodiment, a mouthpiece includes an intraoral component comprising first and second troughs, the troughs substantially vertically aligned and configured to receive a user's upper and lower teeth or upper and lower ridges, the troughs separated by a distance, thereby providing an opening through which the user can breathe; and an extraoral component connected to the intraoral component by first and second columns, the first column positioned between a first end of the intraoral component and a first end of the opening, the second column positioned between a second end of the intraoral component and a second end of the opening, the extraoral component including a first retention portion that extends from the first column away from a center of the intraoral component, the extraoral component further including a second retention portion that extends from the second column away from the center of the intraoral component, the first and second retention portions of the extraoral component configured to contact the user's face.

BRIEF DESCRIPTION OF THE DRAWING(S)

Figure 1:
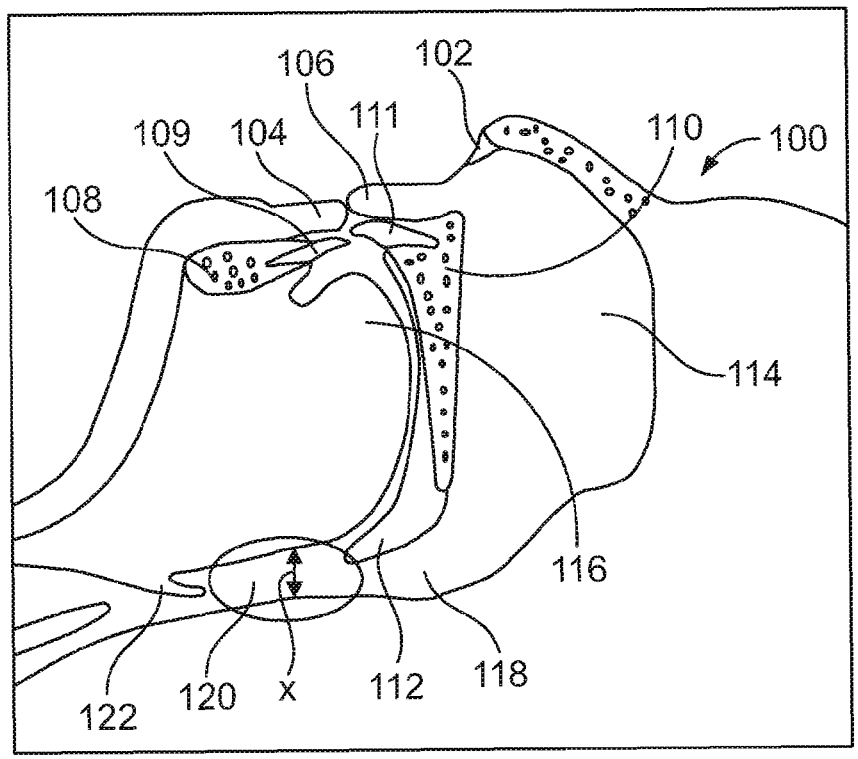
FIG. 1 is a diagram depicting normal anatomy of a human oral cavity, nasal cavity and throat in a supine sleeping position.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF PREFERRED EMBODIMENT(S)

In the figures like elements are identified with like numerals.

FIG. 1 is a diagram 100 depicting normal anatomy of a human oral cavity, nasal cavity and throat in a supine sleeping position. The depicted anatomy includes nostril 102, lower lip 104, upper lip 106, mandible 108, mandibular (lower) teeth 109, hard palate 110, maxillary (upper) teeth 111, soft palate 112, nasal airway 114, tongue 116, nasopaharynx 118, oropharynx 120 and epiglottis 122. In the normal sleeping position, lips 104, 106 are together, teeth 109, 111 are apart, tongue 116 is in the roof of the mouth, and nasal breathing occurs. Note that the airway comprising nasopharynx 118 and oropharynx 120 is open, such that the distance x is sufficient to provide airway patency.

Figure 2:
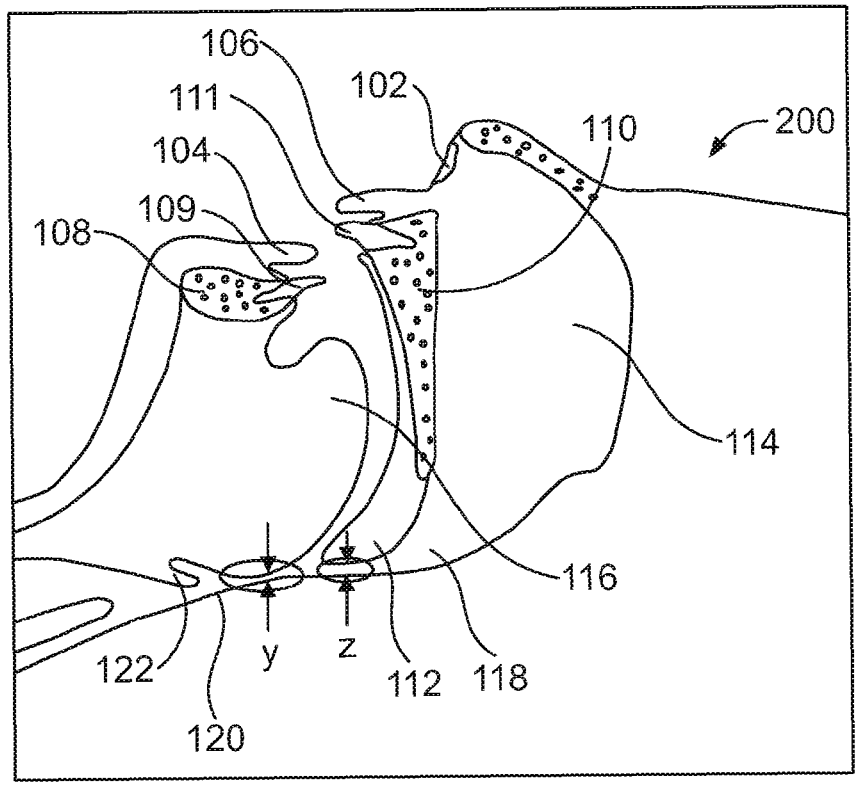
FIG. 2 is a diagram depicting airway anatomy of a human oral cavity, nasal cavity and throat in a supine sleeping position that can result in snoring.

FIG. 2 is a diagram 200 depicting airway anatomy of a human oral cavity, nasal cavity and throat in a supine sleeping position that can result in snoring. Note that the mouth is open, mandible 108 and tongue 116 are closer to the throat, such that distances y and z are less than distance x (from FIG. 1), indicating decreased airway patency. This position can result in vibration of soft tissues, including soft palate 112, and upper airway resistance between oropharynx 120 and nasopaharynx 118.

Figure 3:
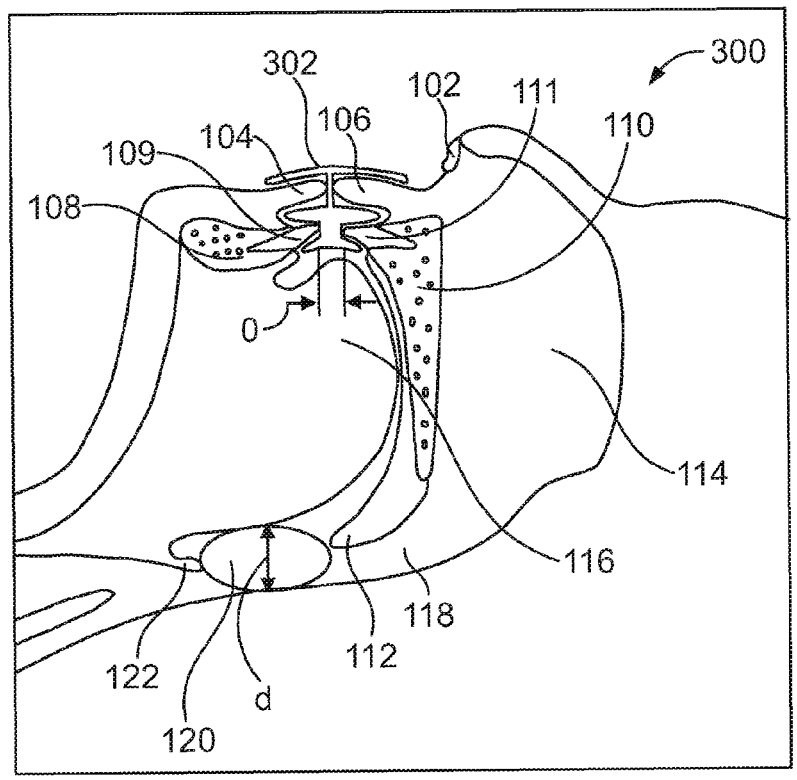
FIG. 3 is a diagram depicting airway anatomy of a human oral cavity, nasal cavity and throat when a mouthpiece used in accordance with embodiments of the present technology is inserted into the mouth.
Figure 4:
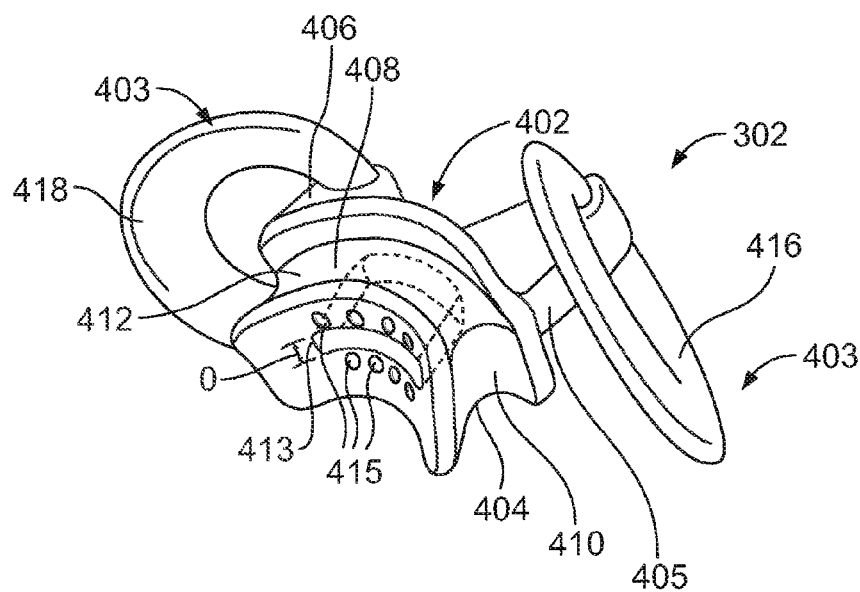
FIG. 4 is a perspective view of a mouthpiece used in accordance with embodiments of the present technology.
Figure 5:
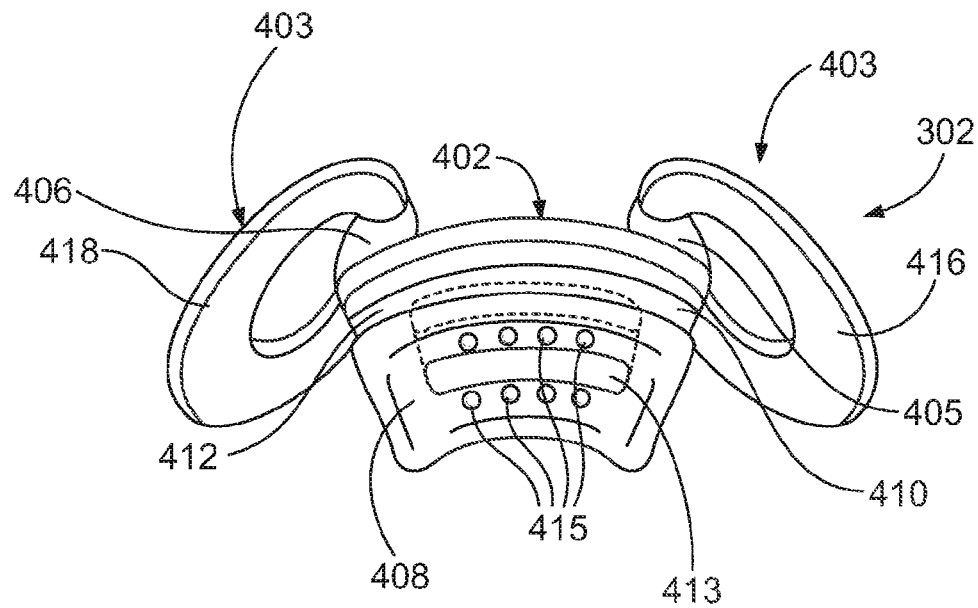
FIG. 5 is a perspective view of the mouthpiece depicted in FIG. 4.
Figure 6:
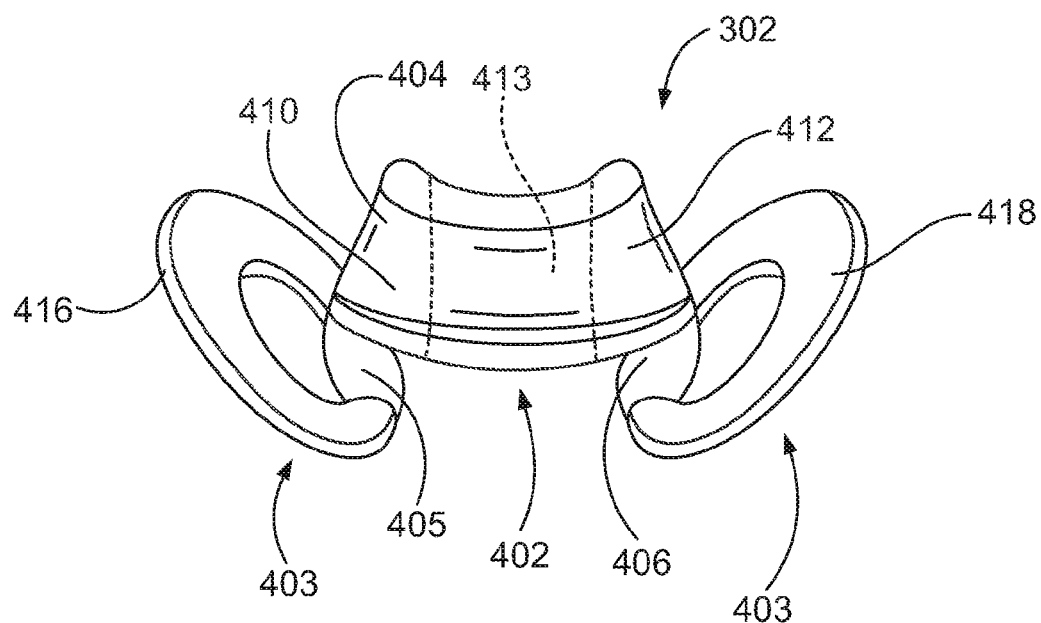
FIG. 6 is a top/bottom view of the mouthpiece depicted in FIG. 4.

FIG. 3 is a diagram 300 depicting airway anatomy of a human oral cavity, nasal cavity and throat when mouthpiece 302 used in accordance with embodiments of the present technology is inserted into the mouth. Mouthpiece 302 can improve oral airway dilation by supporting teeth 109, 111 in an increased vertical interarch opening (indicated as o in FIG. 3) and by advancing mandible 108 and tongue 116 into a more anterior position, such that distance d is sufficient to maintain good airway patency. Mouthpiece 302 can dilate the oral airway both anteroposteriorly and laterally, thus reducing collapsibility. Mouthpiece 302 can eliminate the airflow limitation that is required for snoring and allow more air to enter the lungs with normal breathing effort. When compared to the snoring position depicted in FIG. 2, the FIG. 3 position (with mouthpiece 302 in place) can increase airway patency, and reduce or eliminate vibration of soft tissues and upper airway resistance between oropharynx 120 and nasopharynx 118. This can result in easier breathing, increased oxygen in the blood, uninterrupted sleep, less fatigue and increased energy.

FIGS. 4-8 depict views of mouthpiece 302. Mouthpiece 302 includes an intraoral component 402 and an extraoral component 403. Intraoral component 402 is configured to be received in the mouth, while extraoral component 403 remains outside the mouth. Intraoral component 402 and extraoral component 403 are connected by two anteroposterior, horizontal connector columns 405, 406 configured to extend from intraoral component 402 between a user's lips to extraoral component 403.

Intraoral component 402 includes two vertical arch-shaped troughs 404, 408, set one above the other, and configured to receive a user's anterior maxillary (upper) and anterior mandibular (lower) teeth. Troughs 404, 408 are separated by two vertical support columns 410, 412 positioned near the edges of troughs 404, 408, thereby forming an opening 413 through which oral breathing can be performed while mouthpiece 302 is in place. Oral breathing may be necessary in the case of nasal congestion, for example. Intraoral component 402 can be configured such that vertical support columns 410, 412 are about 6 millimeters tall and opening 413 is about 3-4 millimeters tall and about 17 millimeters wide, for example. Intraoral component 402 can include a plurality of protrusive dots 415 spaced around a lingual side of the opening 413 to act as tongue-position stimulating dots. Intraoral component 402 can include eight to ten such protrusive dots 415, four or five above opening 413 and four or five below opening 413. In the embodiment shown, protrusive dots 415 are spaced about one millimeter between the edges of adjacent dots and about two millimeters between the centers of adjacent dots. In other embodiments, any number of protrusive dots can be spaced around the periphery of opening 413 in any desired increments. Also, the depicted protrusive dots 415 are circular in shape, however, in other embodiments, such protrusive dots can be other shapes, such as rectangular or triangular, for example.

Intraoral component 402 can be configured such that, when a user's teeth are fit in troughs 404, 408, vertical support columns 410, 412 are generally positioned between the user's upper and lower cuspid teeth, and opening 413 is generally positioned between the user's upper and lower lateral and central incisors. Intraoral component 402 can be configured such that it only extends intra-arch between a user's cuspid areas, approximately from a user's right cuspids to the user's left cuspids. The cuspid areas are the areas where canine teeth will generally be located in the mouth. In certain embodiments, spanning from about cuspid area to about cuspid area can avoid unwanted positioning of the tongue down and toward the throat, which can reduce airway patency. It has been found that spanning beyond the cuspid areas, for example, to the molar areas, can reduce the volume of space available in the mouth for the tongue.

Figure 9:
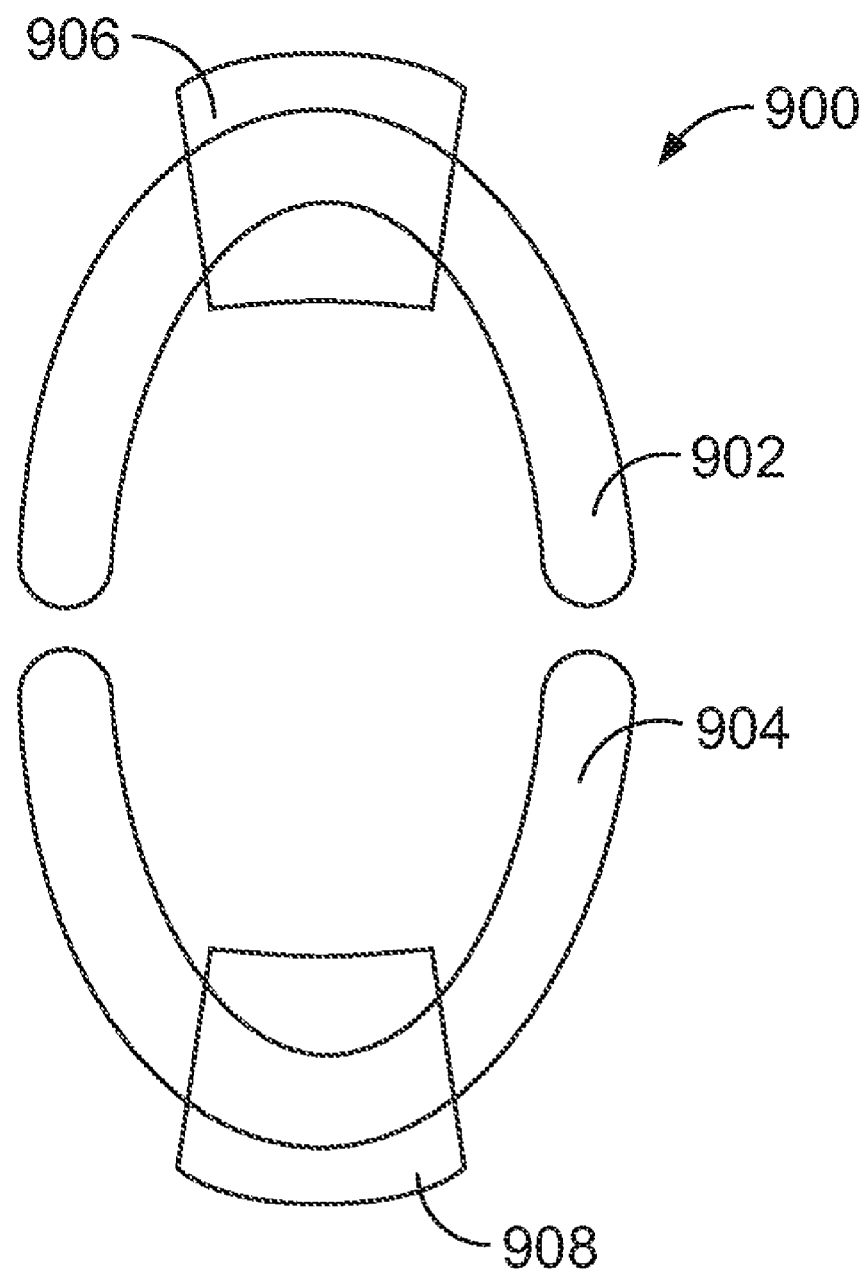
FIG. 9 is a diagram depicting an individual's gums.

As another method of approximation, FIG. 9 provides a diagram 900 depicting a user's gums. The gums include an upper ridge 902 and a lower ridge 904. An approximation of a user's upper anterior ridge is indicated by 906, and an approximation of a user's lower anterior ridge is indicated by 908. The remaining ridge area may be considered posterior. In certain embodiments, spanning only across the user's anterior ridges, and not across the user's posterior ridges, can avoid unwanted manipulation of the tongue down and toward the throat. It has been found that spanning across the user's posterior ridges restricts space in the mouth for the tongue and may cause unwanted positioning of the tongue down and toward the throat.

Embodiments of the present technology can be provided for dentate and edentulous people. Thus, portions of the present application that make reference to specific teeth or teeth areas should be understood as describing the same general area(s) of an edentulous individual's gums. Nonetheless, certain embodiments for edentulous people may extend the span of the intraoral component beyond the anterior ridges, which may be too flabby and floppy to secure the device. For example, such embodiments could extend to the areas where the first or second premolars would be located. Also, embodiments configured for edentulous people can have vertical support columns 410, 412 of increased thickness between troughs 404, 408, thereby accommodating the edentulous ridges and making up for the absence of teeth.

When a user's teeth or anterior ridges are fit in troughs 404, 408, the user's mandible and tongue can be brought forward into a more anterior position. If the user is breathing nasally, the tip of the user's tongue can fill opening 413. This can aid in positioning the tongue toward the roof of the mouth, which is preferred for nasal breathing.

Intraoral component 402 and extraoral component 403 are connected by two anteroposterior, horizontal connector columns 405, 406 configured to extend from intraoral component 402 between a user's lips to extraoral component 403. Horizontal connector columns 405, 406 can be configured to be slightly longer than an average lip thickness, such as 8 millimeters, for example. Horizontal connector columns 405, 406 can be located near the edges of troughs 404, 408, such that they will extend through a user's lips near the lateral borders of the lips at the corners of a user's mouth where the upper lip meets the lower lip. This configuration can allow a user to comfortably close the lips while mouthpiece 302 is in place.

Extraoral component 403 includes two retention portions 416, 418 attached to columns 405, 406 such that each retention portion 416, 418 extends away from opening 413 and away from the center of intraoral component 402. This configuration can allow each retention portion 416, 418 to extend toward a cheek of a user and not block opening 413 and not interfere with nasal breathing or with opening or closing of a user's lips. The retention portions 416, 418 can provide a safety function by keeping intraoral component 402 from being swallowed or aspirated without adversely effecting breathing. Retention portions 416, 418 are flattened oval rings with a thickness of about five millimeters. However, extraoral retention portions can comprise any geometry that extends away from opening 413 and/or away from the center of intraoral component 402, thereby extending toward a cheek of a user so as to maintain the intraoral component 402 in the desired position without blocking opening 413 and/or a user's mouth.

Figure 7:
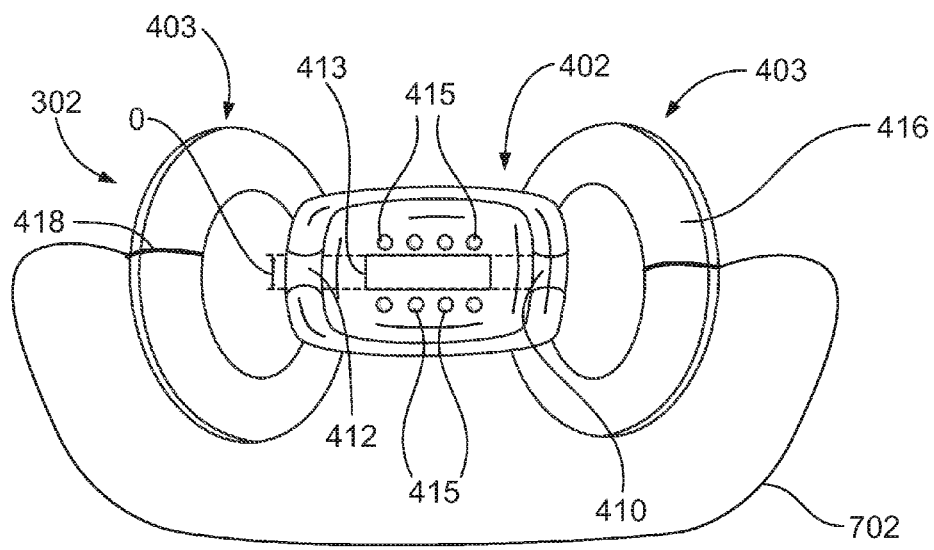
FIG. 7 is a rear view of the mouthpiece depicted in FIG. 4 with a band attached thereto.
Figure 8:
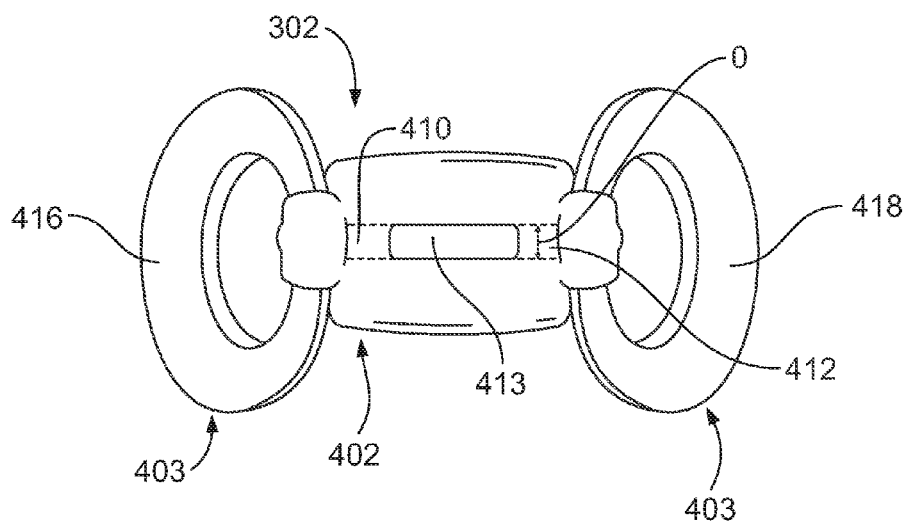
FIG. 8 is a front view of the mouthpiece depicted in FIG. 4.

As depicted in FIG. 7, neck band 702 can be attachable to extraoral component 403. Neck band 702 can be positioned around a user's head in order to maintain intraoral component 402 in the user's mouth during sleep. Neck band 702 can be attached to extraoral component 403 using any suitable method, including by attaching Velcro straps to retention portions 416, 418 that may be rings.

Mouthpiece 302 can be made of medical grade silicone and/or any other suitable material. Mouthpiece 302 can be symmetrical such that either trough 404, 408 can be the upper trough and either trough 404, 408 can be the lower trough. In such embodiments, mouthpiece 302 cannot be inserted upside down.

Certain embodiments for user's with teeth are provided for temporary usage, such as about three months, for example, in order to avoid any appreciable shifting of teeth.

While particular elements, embodiments and applications of the present invention have been shown and described, it will be understood that the invention is not limited thereto since modifications can be made by those skilled in the art without departing from the scope of the present disclosure, particularly in light of the foregoing teachings.

What is claimed is:

1. A mouthpiece comprising:
    an intraoral component comprising:
        an upper trough extending from a first lateral end to a second lateral end and configured to receive at least one of a user's upper teeth or upper ridge, and
        a lower trough extending from a first lateral end to a second lateral end and configured to receive at least one of the user's lower teeth or lower ridge,
        wherein the troughs are substantially vertically aligned, and
        wherein the troughs are separated by a distance, thereby providing an opening through which the user can breathe;
    a first retention portion that extends away from a center of the intraoral component in a first lateral direction;
    a second retention portion that extends laterally away from the center of the intraoral component in a second lateral direction opposite from the first lateral direction, wherein the first and second retention portions of the extraoral component are configured to contact the user's face;
    a first column connecting the first retention portion with the intraoral component, wherein the first column is positioned near the first lateral end of the upper trough and the first lateral end of the lower trough; and
    a second column connecting the second retention portion with the intraoral component, wherein the second column is positioned near the second lateral end of the upper trough and the second lateral end of the lower trough.

2. The mouthpiece of claim 1, wherein the troughs are configured to span only between the user's cuspid teeth areas.

3. The mouthpiece of claim 1, wherein the troughs are configured to span only across the user's anterior ridges, and not to span across the user's posterior ridges.

4. The mouthpiece of claim 1, wherein the first column is positioned between the user's upper and lower cuspid teeth area on a first side of the user's mouth, and the second column is positioned between the user's upper and lower cuspid teeth area on the other side of the user's mouth.

5. The mouthpiece of claim 1, wherein the opening is positioned between the user's upper and lower cuspid teeth areas.

6. The mouthpiece of claim 1, wherein the first and second retention portions each comprise a ring.

7. The mouthpiece of claim 1, wherein the first and second columns each extend a length between the intraoral component and the extraoral component, the length being sufficient to accommodate the thickness of the user's lips, the length being greater than about 8 millimeters.

8. The mouthpiece of claim 1, wherein the first and second columns each extend from a corner of the user's mouth.

9. The mouthpiece of claim 1, further including a first vertical support column and a second vertical support column configured to separate the troughs by the distance.

10. The mouthpiece of claim 1, wherein the intraoral component includes a plurality of protrusive dots about the periphery of a lingual side of the opening.

11. The mouthpiece of claim 1, further including a band attachable to the extraoral component, the band configured to maintain the intraoral component in the user's mouth during sleep.

12. The mouthpiece of claim 1, wherein the mouthpiece is symmetrical such that either trough can accommodate the user's upper teeth or ridge and either trough can accommodate the user's lower teeth or ridge.

13. The mouthpiece of claim 1, wherein the extraoral component does not interfere with the user's ability to open or close the user's lips.

14. The mouthpiece of claim 1, wherein the positioning of the user's upper and lower teeth or ridges in the troughs provides for improved airway patency, such that the user's airway is larger than when the user's mandible is in a normal sleep position.

15. A mouthpiece comprising:
    an intraoral component comprising:
        an upper trough extending from a first lateral end to a second lateral end and configured to receive at least one of a user's upper teeth or upper ridge, and
        a lower trough extending from a first lateral end to a second lateral end and configured to receive at least one of the user's lower teeth or lower ridge,
        wherein the troughs are substantially vertically aligned, and
        wherein the troughs are separated by a distance, thereby providing an opening through which the user can breathe;
    a first retention portion that extends away from the opening in a first lateral direction;

a second retention portion that extends laterally away from the opening component in a second lateral direction opposite from the first lateral direction, wherein the first and second retention portions of the extraoral component are configured to contact the user's face;

a first column connecting the first retention portion with the intraoral component, wherein the first column is positioned near a first lateral end of the opening; and a second column connecting the second retention portion with the intraoral component, wherein the second column is positioned near a second lateral end of the opening.

16. The mouthpiece of claim 15, wherein the troughs are configured to span only between the user's cuspid teeth areas.

17. The mouthpiece of claim 15, wherein the first column is positioned between the user's upper and lower cuspid teeth area on a first side of the user's mouth, and the second column is positioned between the user's upper and lower cuspid teeth area on the other side of the user's mouth.

18. The mouthpiece of claim 15, wherein the first and second retention portions each comprise a ring.

19. The mouthpiece of claim 15, wherein the first and second columns each extend from a corner of the user's mouth.

20. A mouthpiece comprising:

an intraoral component comprising:

an upper trough extending from a first lateral end to a second lateral end and configured to receive at least one of a user's upper teeth or upper ridge, and a lower trough extending from a first lateral end to a second lateral end and configured to receive at least one of the user's lower teeth or lower ridge, wherein the troughs are substantially vertically aligned, and wherein the troughs are separated by a distance, thereby providing an opening through which the user can breathe;

a first retention portion that extends away from a center of the intraoral component in a first lateral direction;

a second retention portion that extends laterally away from the center of the intraoral component in a second lateral direction opposite from the first lateral direction, wherein the first and second retention portions of the extraoral component are configured to contact the user's face;

a first column connecting the first retention portion with the intraoral component, wherein the first column is positioned between a first lateral end of the intraoral component and a first lateral end of the opening; and a second column connecting the second retention portion with the intraoral component, wherein the second column is positioned between a second lateral end of the intraoral component and a second lateral end of the opening.

* * * * *